United States Patent
Helm et al.

(10) Patent No.: US 10,191,615 B2
(45) Date of Patent: Jan. 29, 2019

(54) METHOD AND APPARATUS FOR IMAGE-BASED NAVIGATION

(71) Applicant: Medtronic Navigation, Inc., Louisville, CO (US)

(72) Inventors: Patrick A. Helm, Milton, MA (US); Andrew Bzostek, Boulder, CO (US); James Dustin Duckett, Broomfield, CO (US); Steven L. Hartmann, Superior, CO (US); Robert Teichman, Lafayette, CO (US); David E. Macht, Littleton, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 129 days.

(21) Appl. No.: 15/141,331

(22) Filed: Apr. 28, 2016

(65) Prior Publication Data

US 2017/0316561 A1   Nov. 2, 2017

(51) Int. Cl.
| | |
|---|---|
| *G06K 9/00* | (2006.01) |
| *G06F 3/0481* | (2013.01) |
| *G06K 9/46* | (2006.01) |
| *G06T 7/00* | (2017.01) |
| *G06T 11/60* | (2006.01) |
| *A61B 34/20* | (2016.01) |
| *A61B 34/10* | (2016.01) |

(52) U.S. Cl.
CPC .......... *G06F 3/04817* (2013.01); *A61B 34/20* (2016.02); *G06K 9/4671* (2013.01); *G06T 7/004* (2013.01); *G06T 7/0012* (2013.01); *G06T 11/60* (2013.01); *A61B 2034/102* (2016.02); *A61B 2034/107* (2016.02); *A61B 2034/2051* (2016.02); *G06T 2207/10004* (2013.01)

(58) Field of Classification Search
CPC ... G06F 3/04817; G06K 9/4671; G06T 11/60; G06T 2207/10004; G06T 7/0012; G06T 7/004

See application file for complete search history.

(56) References Cited

U.S. PATENT DOCUMENTS

| | | | |
|---|---|---|---|
| 5,913,820 A | 6/1999 | Bladen et al. | |
| 5,983,126 A | 11/1999 | Wittkampf | |
| 6,235,038 B1 | 5/2001 | Hunter et al. | |
| 6,474,341 B1 | 11/2002 | Hunter et al. | |
| 6,636,757 B1 | 10/2003 | Jascob et al. | |

(Continued)

OTHER PUBLICATIONS

International Search Report and Written Opinion dated Jul. 17, 2017 in corresponding International Application No. PCT/US2017/029906.

(Continued)

*Primary Examiner* — Tom Y Lu
(74) *Attorney, Agent, or Firm* — Harness, Dickey & Pierce, P.L.C.

(57) ABSTRACT

A system and method for a procedure that can be performed on an appropriate subject. Procedures can include assembling any appropriate work piece or installing members into a work piece, such as an airframe, autoframe, etc. Regardless of the subject, generally the procedure can have a selected result that is efficacious. The efficacious result may be the desired placement of a device. The system and method can be used in confirming an efficacious result.

23 Claims, 8 Drawing Sheets

(56) References Cited

U.S. PATENT DOCUMENTS

| | | |
|---|---|---|
| 6,747,539 B1 | 6/2004 | Martinelli |
| 6,940,941 B2 | 9/2005 | Gregerson et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 7,751,865 B2 | 7/2010 | Jascob et al. |
| 7,792,032 B2 | 9/2010 | Dobson et al. |
| 7,797,032 B2 | 9/2010 | Martinelli et al. |
| 8,010,177 B2 | 8/2011 | Csavoy et al. |
| 8,644,907 B2 | 2/2014 | Hartmann et al. |
| 8,842,893 B2 | 9/2014 | Teichman et al. |
| 8,977,021 B2 * | 3/2015 | Kang ............... G16H 50/50 382/128 |
| 9,706,948 B2 * | 7/2017 | Bhandari ........... A61B 5/1114 |
| 9,785,246 B2 * | 10/2017 | Isaacs ................ G06F 3/017 |
| 2004/0199072 A1 | 10/2004 | Sprouse et al. |
| 2008/0089566 A1 | 4/2008 | Node-Langlois et al. |
| 2008/0200794 A1 * | 8/2008 | Teichman ........... A61B 90/39 600/407 |
| 2010/0138183 A1 * | 6/2010 | Jensen ................ A61G 13/10 702/150 |
| 2010/0153076 A1 * | 6/2010 | Bellettre ............. G06T 19/00 703/2 |
| 2010/0228117 A1 | 9/2010 | Hartmann |
| 2011/0268325 A1 | 11/2011 | Teichman et al. |
| 2013/0211792 A1 * | 8/2013 | Kang ................ G06F 19/3437 703/1 |

OTHER PUBLICATIONS

Sautot, "Vissage Pediculaire Assiste Par Ordinateur," 4 pages—Sep. 20, 1994.

International Preliminary Report on Patentability dated Nov. 8, 2018 in corresponding International Application No. PCT/US2017/029906.

* cited by examiner

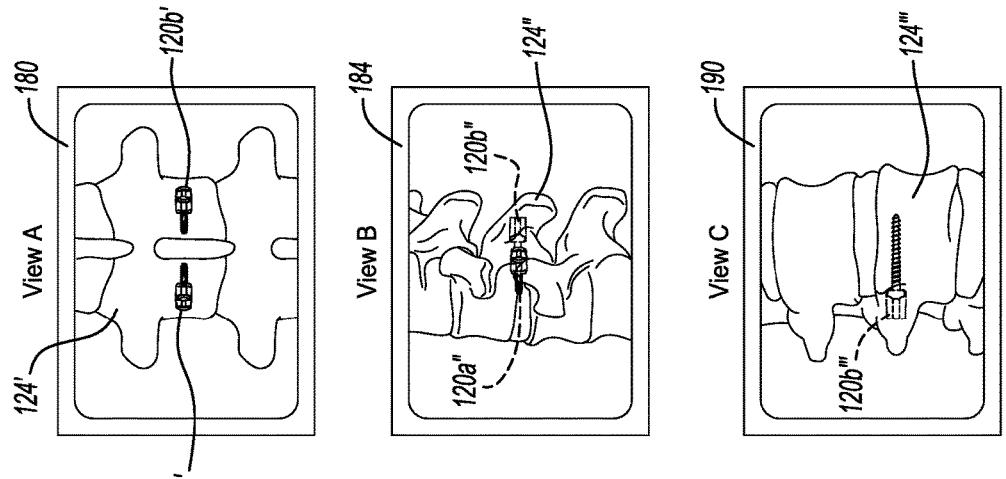
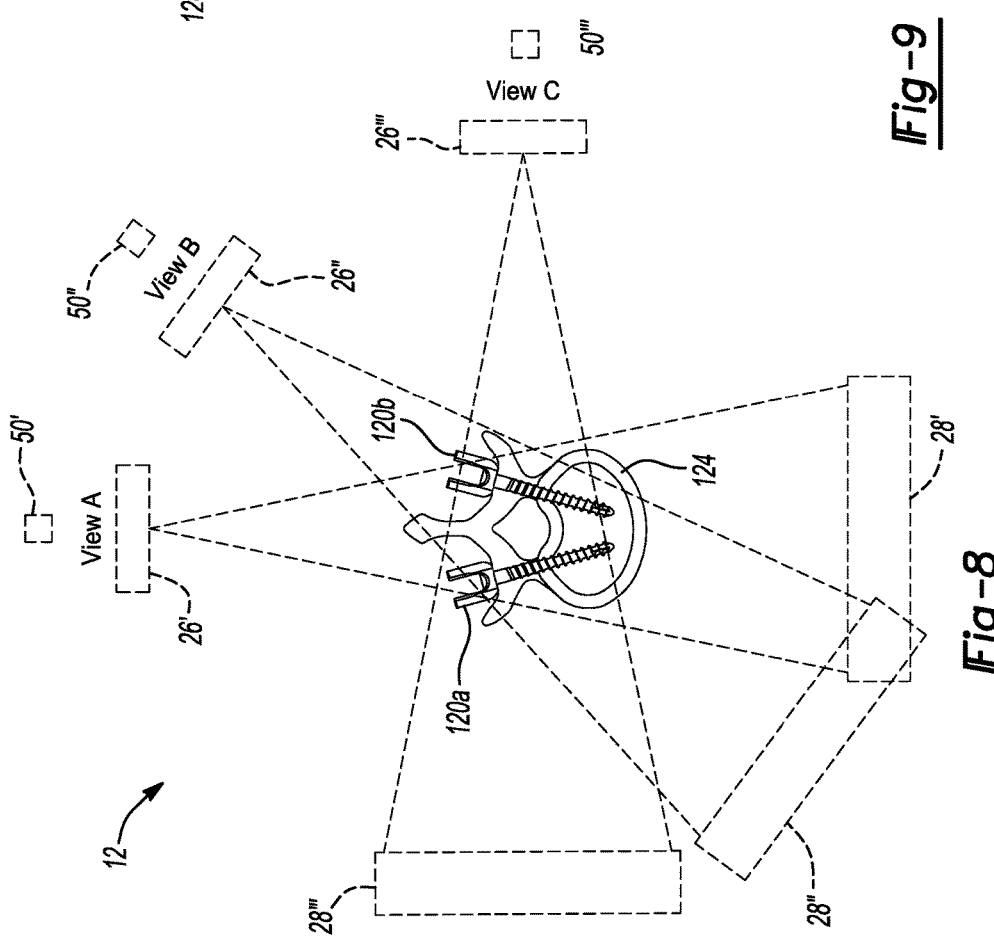

METHOD AND APPARATUS FOR IMAGE-BASED NAVIGATION

FIELD

The subject disclosure relates to a system for performing a procedure, and exemplarily relates to a system to incorporate imaging of a subject during performing a surgical procedure on a subject.

BACKGROUND

This section provides background information related to the present disclosure which is not necessarily prior art.

The images of a subject may be acquired prior to a procedure and intra- or post-operatively or post-procedurally. For example, image data can be acquired of a patient and a three-dimensional model of the subject can be generated based upon the acquired image data. The three-dimensional model can be used for various purposes, such as planning a procedure on the subject including selecting an implant (if an implant is to be positioned in the subject), determining entry points, and/or trajectories for performing a procedure and/or implantation, and other selected planning features. Further, the planning can include determining placement of a selected implant, such as a lead electrode for a cardiac system (e.g., a cardiac synchronization system) or a lead for a brain stimulation system. Accordingly, it is understood that the image data newly acquired for performing a procedure in soft tissue and/or hard tissue. Various procedures may also require performing a procedure in both hard and soft tissue.

The system and method disclosed herein can then be used to assist in verifying the selected plan and/or determining a final position of an implant. Various predetermined models of an implant along with tracked information of an implant can be used to assist in analyzing intra-procedure or post-procedure image data to determine a final position of an implant. Further, the system, in particular with navigation or testing images can be used to determine positioning of an imaging system for acquiring image data of the subject after acquiring the initial image data, such as the image data acquired procedurally.

SUMMARY

This section provides a general summary of the disclosure, and is not a comprehensive disclosure of its full scope or all of its features.

A system and/or method is disclosed that can be used to confirm or determine a position of an implant. During a procedure, such as a surgical procedure, an implant or member can be placed in a subject. After a certain time during the procedure or after the procedure is complete (e.g. an implant or part of an implant system are placed), an image can be acquired of the subject. A pre-formed model (such as a computer aided or assisted design (CAD) model) can be overlayed or superimposed on the acquired image data at the determined location of the implanted member to assist in confirming placement of the implant. The overlayed image can be used to confirm completion of a planned procedure as well.

An imaging system can be used to acquire images of the subject, such as a human patient, before the initiation of the procedure, during the procedure, and after completion of at least a portion of the procedure. Images acquired of a subject prior to initiating a procedure may be used to assist in planning the procedure, such as selecting a trajectory for the procedure and selecting an implant. Images acquired during a procedure may include those acquired after an initial incision and/or partial placement of an implant and images acquired to assure that the procedure is progressing according to a predetermined plan. The procedure can include implantation of an implant including an insertion of an implant through an incision and forming an incision.

Images may also be acquired after the procedure is complete to confirm appropriate or selected placement of the implant. The after procedure images may be used to confirm that a procedure has been completed, as planned prior to beginning the procedure. The planned procedure may be based on the initial image data. Further, the after procedure images may be used by a user to determine if further procedure steps are useful or necessary.

It is understood by one skilled in the art that implants may include boney implants, soft tissue implants, or the like. Boney implants may include implants such as medical screws or joint replacement portions. Soft tissue implants may include stents or placements of leads, such as cardiac pacing leads or deep brain stimulation leads. Further, procedures may include ablation procedures or soft tissue resection procedures.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 8 is a schematic view of the imaging device in various positions relative to a patient;

FIG. 9 is a schematic representation of images based on image data acquired at the various positions illustrated in FIG. 8.

Corresponding reference numerals indicate corresponding parts throughout the several views of the drawings.

DETAILED DESCRIPTION

Example embodiments will now be described more fully with reference to the accompanying drawings.

Figure 1:
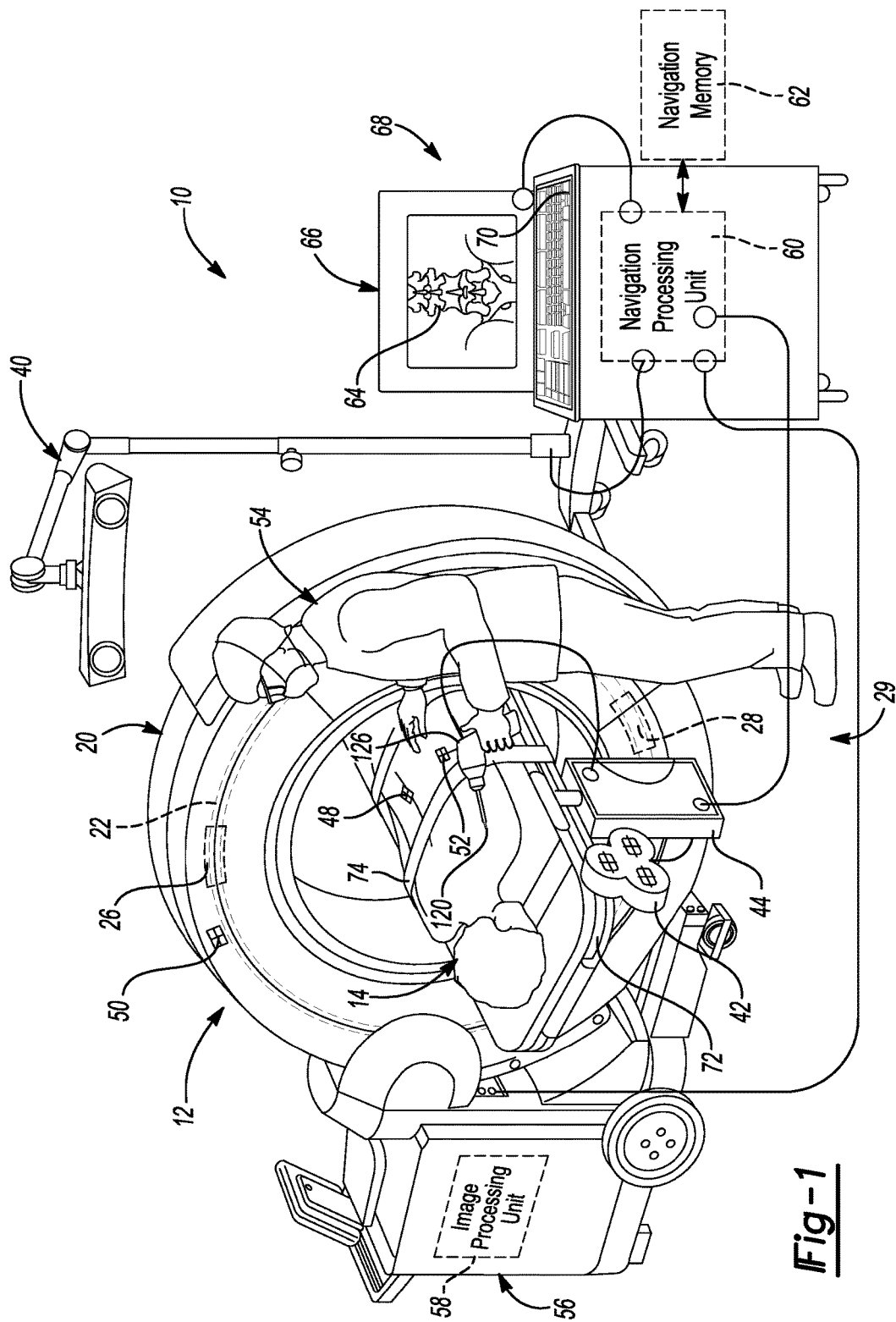
FIG. 1 is an environmental view of an operating theatre including an optional imaging system and a navigation system.

FIG. 1 is a diagram illustrating an overview of a navigation system 10 that can be used for various procedures. The navigation system 10 can be used to track the location of an item, such as an implant or an instrument (as discussed herein), relative to a subject, such as a patient 14. It should further be noted that the navigation system 10 may be used to navigate any type of instrument, implant, or delivery system, including: guide wires, arthroscopic systems, orthopedic implants, spinal implants, deep brain stimulation (DBS) leads, cardiac pacing leads, ablation instruments, etc. Moreover, the instruments may be used to navigate or map any region of the body. The navigation system 10 and the various tracked items may be used in any appropriate procedure, such as one that is generally minimally invasive or an open procedure.

The navigation system 10 can interface with an imaging system 12 that is used to acquire pre-operative, intra-operative, or post-operative, or real-time image data of the patient 14. It will be understood by one skilled in the art, any appropriate subject can be imaged and any appropriate procedure may be performed relative to the subject. The subject may be a human patient and the procedure may be a surgical procedure, such as an implantation of a device (e.g. a screw, lead, etc.).

Exemplarily illustrated in FIG. 1, the imaging system 12 comprises an O-Arm® imaging device sold by Medtronic Navigation, Inc. having a place of business in Louisville, Colo., USA. The imaging device 12 may have a generally annular gantry housing 20 that encloses an image capturing portion 22. The image capturing portion 22 may include an x-ray source or emission portion 26 and an x-ray receiving or image receiving portion 28 located generally or as practically possible 180 degrees from each other within the gantry housing 20. In various embodiments, the x-ray source or emission portion 26 and the x-ray receiving or image receiving portion 28 may be mounted on a rotor (not illustrated) relative to a track (not illustrated) within the generally annular gantry housing 20. The image capturing portion 22 can be operable to rotate 360 degrees during image acquisition. The image capturing portion 22 may rotate around a central point or axis, allowing image data of the patient 14 to be acquired from multiple directions or in multiple planes. The imaging system 12 can include those disclosed in U.S. Pat. Nos. 7,188,998; 7,108,421; 7,106,825; 7,001,045; and 6,940,941; all of which are incorporated herein by reference. The imaging system 12, however, may also include or be replaced with other imaging systems including C-arm fluoroscopic imaging systems, computer tomography (CT) imaging systems, etc. which can also generate three-dimensional views of the patient 14.

The position of the image capturing portion 22 can be precisely known relative to any other portion of the imaging device 12. In addition, as discussed herein, the precise knowledge of the position of the image capturing portion 22 can be used in conjunction with a tracking system 29 to determine the position of the image capturing portion 22 and the image data relative to the subject, such as the patient 14, which is tracked. For example a patient tracking device 48 may be placed on the patient 14 to track the patient 14.

The tracking system 29 can include various portions that are associated or included with the navigation system 10. The tracking system 29 can also include a plurality of types of tracking systems including an optical tracking system that includes an optical localizer 40 and/or an electromagnetic (EM) tracking system that can include an EM localizer 42. The optical localizer 40 may "view" or optically track trackable portions (tracking devices) with cameras. The EM localizer 42 may generate a field and a trackable portion (e.g. EM tracking device) may sense the field to determination a location relative to another tracking device in the field. Various tracking devices, including those discussed further herein, can be tracked with the tracking system 29 and the information can be used by the navigation system 10 to allow for a display of a position of an item. Briefly, tracking devices, such as a patient tracking device 48, an imaging device tracking device 50, and an instrument tracking device 52, allow selected portions of an operating theater to be tracked relative to one another with the appropriate tracking system 29, including the optical localizer 40 and/or the EM localizer 42.

It will be understood that any of the tracking devices 48-52 can be optical or EM tracking devices, or both, depending upon the tracking localizer used to track the respective tracking devices. It will be further understood that any appropriate tracking system can be used with the navigation system 10. Alternative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 8,644,907, issued Feb. 4, 23012, titled "Method And Apparatus For Surgical Navigation"; U.S. Pat. No. 7,751,865, titled "Method And Apparatus For Surgical Navigation", issued Jul. 6, 2010; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated by reference herein.

Further, for EM tracking systems it may be necessary to provide shielding or distortion compensation systems to shield or compensate for distortions in the EM field generated by the EM localizer 42. Exemplary shielding systems include those in U.S. Pat. No. 7,797,032, titled "Method and system for navigating a catheter probe in the presence of field-influencing objects", issued on Sep. 14, 2010 and U.S. Pat. No. 6,747,539, titled "Patient-shielding and coil system", issued on Jun. 8, 2004, all of which are incorporated herein by reference. Distortion compensation systems can include those disclosed in U.S. Pat. No. 6,636,757, titled "Method and apparatus for electromagnetic navigation of a surgical probe near a metal object", issued on Oct. 21, 2003, all of which are incorporated herein by reference.

With an EM tracking system, the EM localizer 42 and the various tracking devices can communicate through an EM controller 44. The EM controller can include various amplifiers, filters, electrical isolation, and other systems. The EM controller 44 can also control the coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TRIA®, TREON®, and/or S7™ Navigation System having an optical localizer, similar to the optical localizer 40, sold by Medtronic Navigation, Inc. having a place of business in Louisville, Colo. Optical tracking systems may also include those discloses in U.S. Pat. No. 8,010,177, Aug. 30, 2011, Intraoperative Image Registration"; U.S. Pat. No. 6,235,038, issued on May 22, 2001, titled "System For Translation Of Electromagnetic And Optical Localization Systems", all incorporated herein by reference. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 12 can include a support housing or cart 56. The imaging system 12 can further include a separate image processing unit 58 that can be housed in the cart 56. The navigation system 10 can include the navigation processing unit 60 that can communicate or include a navigation memory 62. The navigation member 62 may include any appropriate non-transitory memory including a random access memory, magnetic media drive, etc. Further, the navigation memory 62 may be integrated with the navigation processing unit 60 or remote from the navigation processing unit 60. The navigation processing unit 60 can receive information, including image data, from the imaging system 12 and tracking information from the tracking systems 29, including the respective tracking devices 48-52 and the localizers 40-42. Image data can be displayed as an image 64 on a display device 66 of a workstation or other computer system 68. The workstation 68 can include appropriate input devices, such as a keyboard 70. It will be understood that other appropriate input devices can be included, such as a mouse, a foot pedal or the like. The various processing units and computers or workstations may include internal or local memory and processing units. The processing units may include central processing units that are general computers that execute instructions to perform tasks on a chip. The processing units may also be specific circuits, such as application specific integrated circuits (ASIC). Accordingly, the processing units may be devices that receive information and execute instructions that are stored or received based on the information.

The image processing unit 58 processes image data from the imaging system 12 and transmits it to the navigation processing unit 60. It will be further understood, however, that the imaging system 12 need not perform any image processing and it can transmit the image data directly to the navigation processing unit 60. Accordingly, the navigation system 10 may include or operate with a single or multiple processing centers or units that can access single or multiple memory systems based upon system design.

The patient 14 can be fixed onto an operating table 72, but is not required to be fixed to the table 72. The table 72 can include a plurality of straps 74. The straps 74 can be secured around the patient 14 to fix the patient 14 relative to the table 72. Various apparatuses may be used to position the patient 14 in a static position on the operating table 72. Examples of such patient positioning devices are set forth in commonly assigned U.S. patent application Ser. No. 10/405,068, published as U.S. Pat. App. Pub. No. 2004/0199072, entitled "An Integrated Electromagnetic Navigation And Patient Positioning Device", filed Apr. 1, 2003, which is hereby incorporated by reference. Other known apparatuses may include a Mayfield® clamp.

Also, the position (including three-dimensional location and orientation) of the patient 14 relative to the imaging system 12 can be determined by the navigation system 10 with the patient tracking device 48 and the imaging system tracking device 50. As discussed herein, the position (including three-dimensional location and orientation) relative to the patient 14 may be determined, at least in part, with images acquired of the patient 14. Accordingly, the position (including three-dimensional location and orientation) of the patient 14 relative to the imaging system 12 can be determined. The imaging system 12, such as the O-Arm® can know its position and be repositioned to the same position within about 10 microns. This allows for a substantially precise placement of the imaging system 12 and precise determination of the position of the imaging device 12. Precise positioning of the imaging portion 22 is further described in U.S. Pat. Nos. 7,188,998; 7,108,421; 7,106, 825; 7,001,045; and 6,940,941; all of which are incorporated herein by reference. Generally, it may be selected to determine the position of the image data relative to the patient 14. For example, the position, including the orientation relative to the patient, of the image data may be used to determine a location of a portion of the patient 14.

Subject or patient space and image space can be registered by identifying matching points or fiducial points in the patient space and related or identical points in the image space. The imaging device 12, such as the O-Arm® imaging device sold by Medtronic, Inc., can be used to generate image data at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12 relative to the patient 14. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, now published U.S. Pat. App. Pub. No. 2010/0228117, incorporated herein by reference.

Once registered, the navigation system 10 with or including the imaging system 12, can be used to perform selected procedures. Selected procedures can use the image data generated or acquired with the imaging system 12. Further, the imaging system 12 can be used to acquire image data at different times relative to a procedure. As discussed herein, image data can be acquired of the patient 14 subsequent to a selected portion of a procedure for various purposes, including confirmation of the portion of the procedure.

With continuing reference to FIG. 1, the imaging system 12 can generate actual or virtual three dimensional images of the patient 14. The patient 14 can be placed relative to the imaging system 12 to allow the imaging system 12 to obtain image data of the patient 14. To generate 3D image data, the image data can be acquired from a plurality of views or positions relative to the patient 14. The 3D image data of the patient 14 can be used alone or with other information to assist in performing a procedure on the patient 14 or an appropriate subject. It will be understood, however, that any appropriate imaging system can be used, including magnetic resonance imaging, computed tomography, fluoroscopy, etc. to acquire image data (including 3D image data) of the patient 14.

Figure 2:
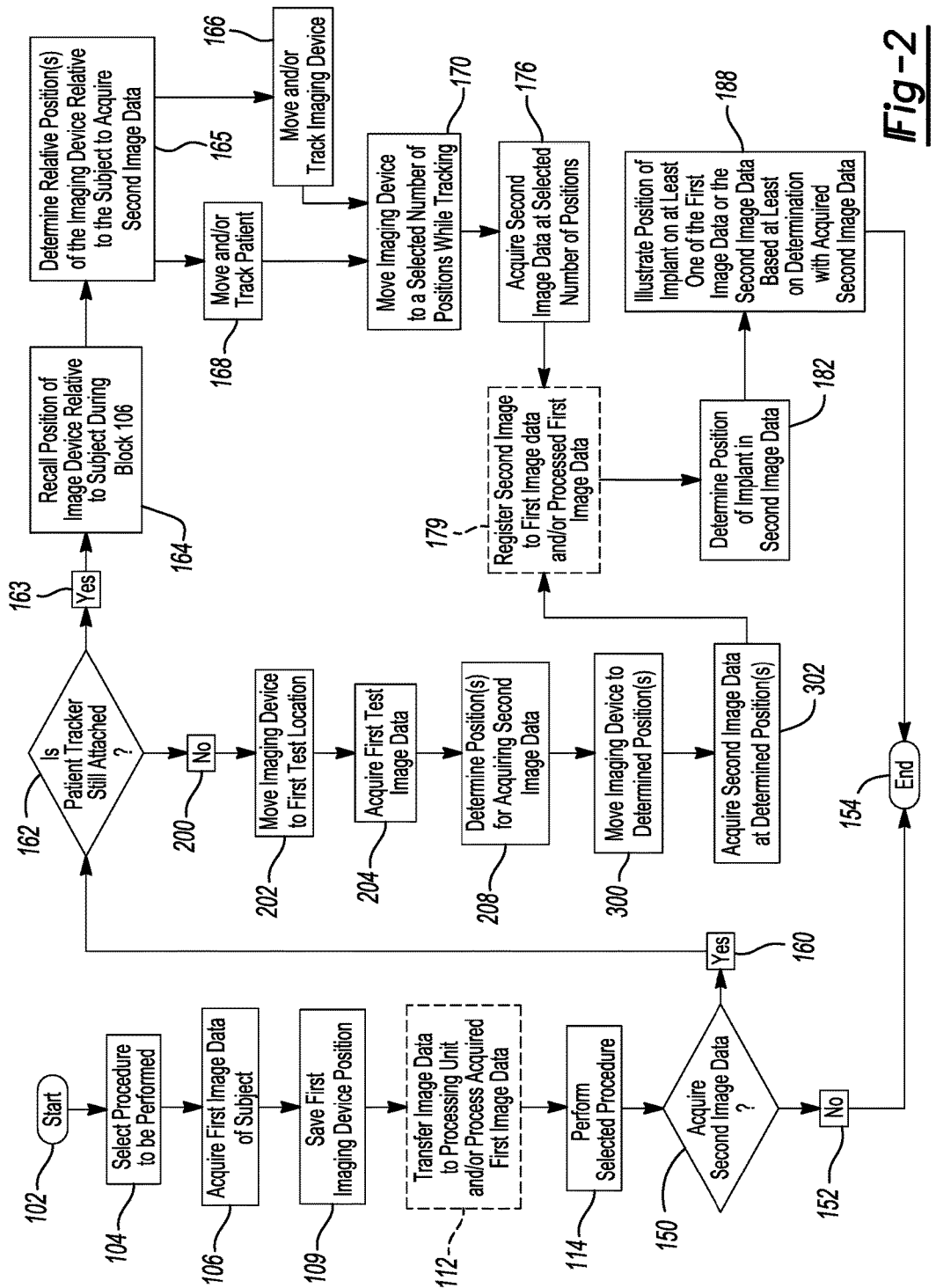
FIG. 2 is a flow chart illustrating a procedure for performing and confirming placement of an implant in a patient.

With initial reference to FIG. 2, a flow chart 100 illustrates a method for confirming placement of an implant after an implantation procedure, as illustrated in FIGS. 3-10. It will be understood that although the flowchart 100 describes and is directed to a method of placing a spinal implant, including one or more pedicle screws 120 in a vertebra 124. The method 100, however, may be used to acquire image data to assist in confirming placement of any appropriate implant in any appropriate portion of the anatomy, such as an intramedullary (IM) rod in a long bone (e.g. a femur), a knee or hip replacement prosthesis, or any other appropriate procedure. Accordingly, the method in flowchart 100 will be understood to encompass selected procedures beyond pedicle screw placement. In addition, it will be understood that the method of the flowchart 100 can be used to confirm placement of any appropriate member in any appropriate structure. For example, placement of a member, including a spike, into a radiolucent work piece (e.g. wood board), can also be confirmed with the method in the flowchart 100.

The method in the flowchart 100 can begin at start block 102. A procedure can then be selected in block 104. The procedure can be any appropriate procedure, such as the placement of the pedicle screw within the vertebra 124 (FIG. 6) of a patient 14. It will be understood that the placement of the pedicle screw 120 in the vertebra 124 of the patient 14 can be performed for any appropriate procedure, such as spinal fusion or vertebral rigidity. Regardless of the procedure selected in block 104, a first image data of the subject 14 can be acquired in block 106. The first image data may be acquired, however, prior to the determination of a procedure to be performed. For example, the first image data acquired in block 106 may be initial diagnostic image data that is used to select, confirm, and/or plan the procedure in block 104. The first image data, therefore, may be pre-procedure or pre-acquired image data. The first image data is image data of the patient 14 prior to performing the selected procedure from block 104.

In selecting the procedure to be performed in block 104, a surgical plan may be generated, as understood by one skilled in the art. The surgical plan may include selection of entry positions, trajectories for implantation of implants (e.g. pedicle screws), selection of instruments for performing the procedure, and other appropriate selections and steps for the procedure. The procedure, however, need not be a surgical procedure and may include a plan for carrying out other selected procedures, such as installing or assembling a mechanical assembly (e.g. an automobile).

Figure 3:
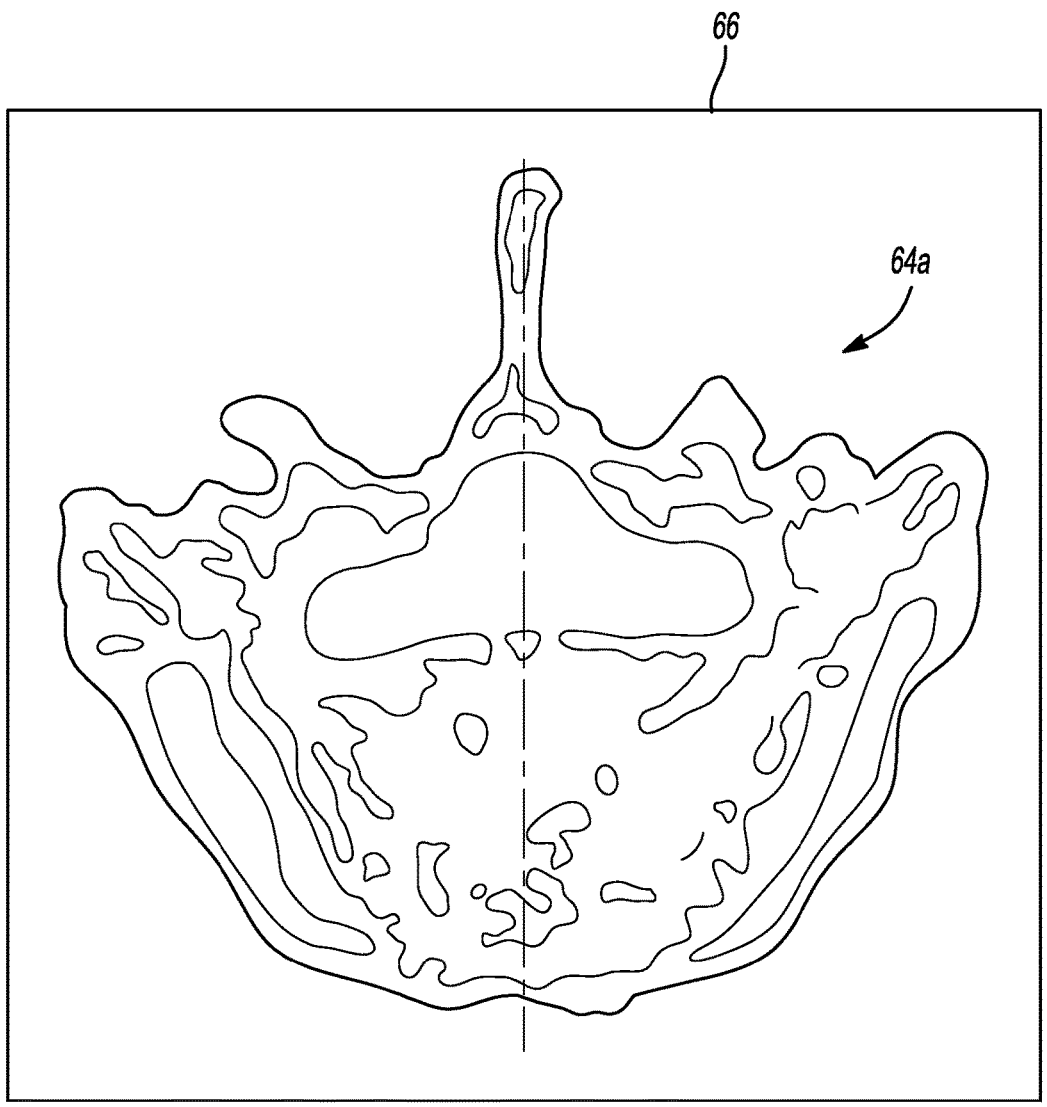
FIGS. 3-5 illustrate image data of a spine of a patient from various perspectives.
Figure 4:
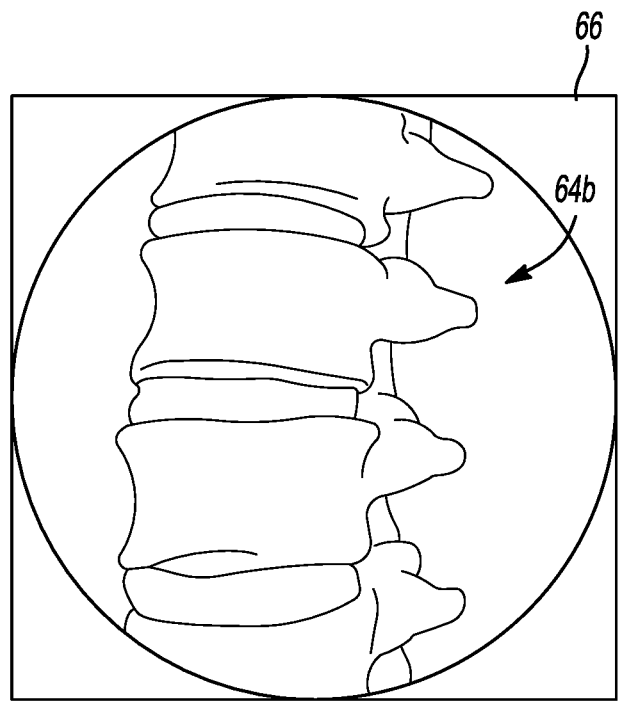
Figure 5:
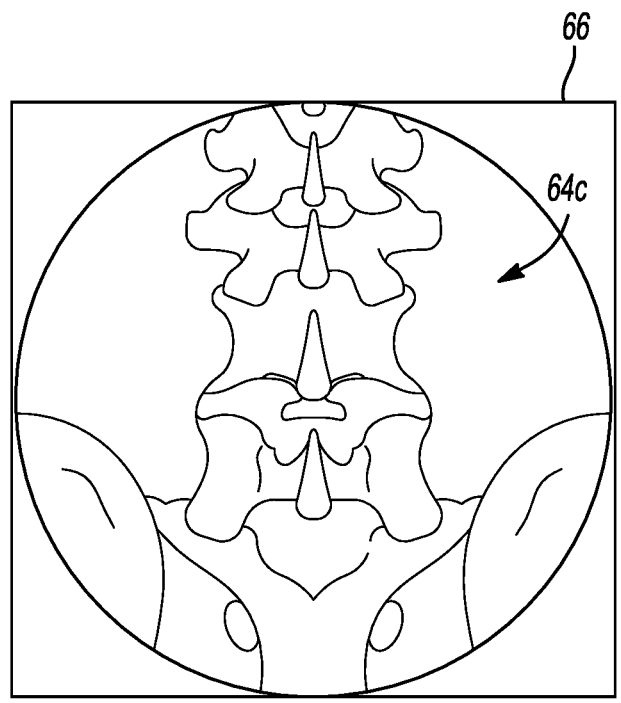

The image data acquired in block 106 can be any appropriate image data, such as x-ray image data of a single vertebra, illustrated in FIG. 3, in a superior viewpoint. The image data may also include an image of a plurality of vertebrae, as illustrated in FIG. 4, from a lateral perspective. Further, the image data may include a posterior perspective of a plurality of vertebrae, as illustrated in FIG. 5. The image data can be displayed on the display 66 as the image 64*a*, 64*b*, 64*c*, respectively, or can be acquired and saved in the memory or storage system 62 of the navigation system 10, can be used for later confirmation of a procedure, or can be used for both.

Briefly, a first image data of the subject can be image data acquired of the subject or the patient 14 prior to any portion of a surgical intervention being performed. For example, the patient 14 can be imaged with the imaging system 12 substantially immediately after entering an operating theater and prior to performing any surgical procedures, such as forming an incision. It will be further understood that the first image data of the subject acquired in block 106 can be acquired at any point prior to the patient 14 entering the surgical theater. Regardless of the timing of acquiring the first image data, the first image data is image data of the patient or subject 14 in a first condition, such as having been unaltered by a surgical procedure. As discussed further herein, in relation to the method in the flowchart 100, this image data can be used along with later or second acquired image data and a model (e.g. a CAD model) of an implant for confirmation of placement of an implant in the patient 14.

As discussed above, however, the image data acquired in block 106 can be acquired at a selected position relative to the patient 14. As illustrated in FIG. 1, the imaging device tracking device 50 can be tracked as can the patient 14 with the patient tracker 48. Thus, the position of the imaging device 12 relative to the patient 14 can be determined with the navigation system 10 when acquiring the first image data in block 106. This first imaging position may be saved in block 109. This first imaging device position saved in block 109 may include a discrete position (including a location and an orientation) for each image portion acquired of the patient 14. For example, a plurality of exposures may be acquired and each exposure may be at a different position relative to the patient 14. Thus, the first imager position saved in block 109 may include a position for each exposure of the imaging device 12 acquired with the first image data. These positions may be saved for later recall, such as being saved in the navigation memory 62.

After the first image data is acquired in block 106, the first image data can be optionally transferred to a data processor in block 112. The image data transferred to the data processor in block 112 can be all first image data acquired of the patient 14 in the first image data from block 106. The first image data from block 106 may be viewed as two-dimensional (2D) projections of the subject 14 or may be used to generate a three-dimensional (3D) model of the subject 14. For example, one of more 2D projections may be processed in block 112 to generate a 3D model of the subject 14. The model may then be viewed as the image on the display. Further, a procedure may be planned with the 3D model and at least a portion of the plan (e.g. selected final implanted locations of members) may be illustrated as icons superimposed on the 3D model and/or 2D projections. As illustrated in FIGS. 3-5, image data can be acquired of the patient 14 from a plurality of perspectives or viewpoints.

The first image data acquired in block 106 can be saved or transferred to any appropriate processing core or system, or can simply be directly transferred or maintained to be accessed by a single processing unit. As discussed above, the imaging processing unit 58 can be incorporated in the imaging system 12 and the navigation processor 60 can be included with the navigation workstation 68. Accordingly, the two processing units can communicate and image data can be transferred therebetween. Alternatively, the image data can be simply acquired and transferred to the navigation processor 60. Regardless, it will be understood that the navigation system 10 can process the image data with a single or multiple processing unit or cores as understood by one skilled in the art.

Figure 6:
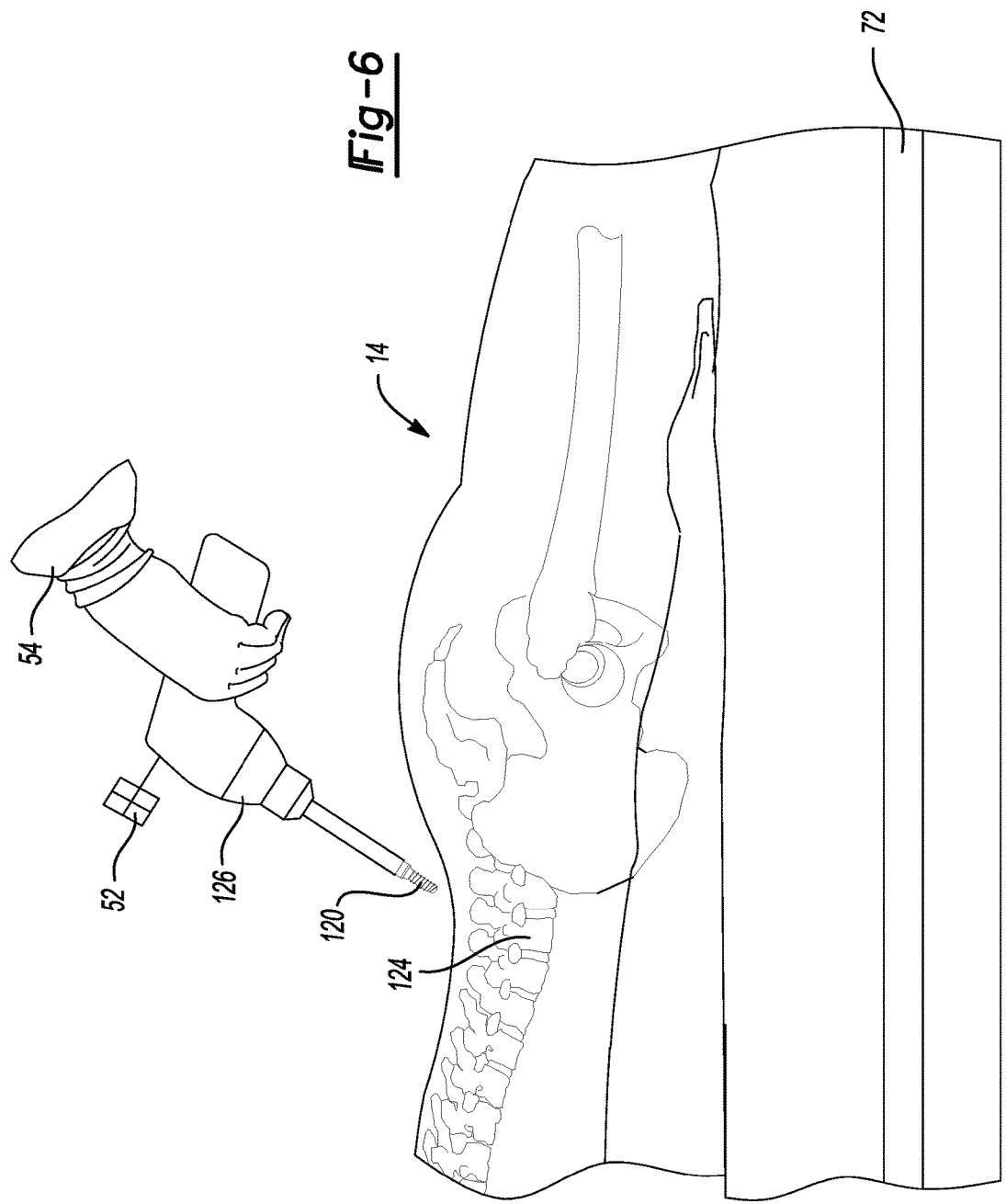
FIG. 6 is a schematic illustration of an instrument for inserting an implant into a patient.

Once the first image data is acquired in block 106 and optionally transferred to a processor in block 112, the selected procedure can be performed in block 114. As illustrated in FIG. 6, the procedure can include placement of a pedicle screw 120 into the patient 14. As is generally understood, the anatomy of the patient 14 can include the vertebra 124 into which the pedicle screw 120 can be positioned or implanted. The pedicle screw 120 can be implanted with an appropriate surgical instrument, such as surgical motor 126 or can be implanted with an appropriate manual driver (not illustrated) such as the CD Horizon® Legacy™ System manual driver, sold by Medtronic Spine and Biologics having a place of business in Minneapolis, Minn. Regardless of the instrument used to implant the pedicle screw 120, the instrument and/or the pedicle screw 120 can include a tracking device 52. The tracking device 52 can be tracked by the navigation system 10, such as with either or both of the tracking systems including the optical localizer 40 or the EM localizer 42 during the surgical procedure.

Figure 7:
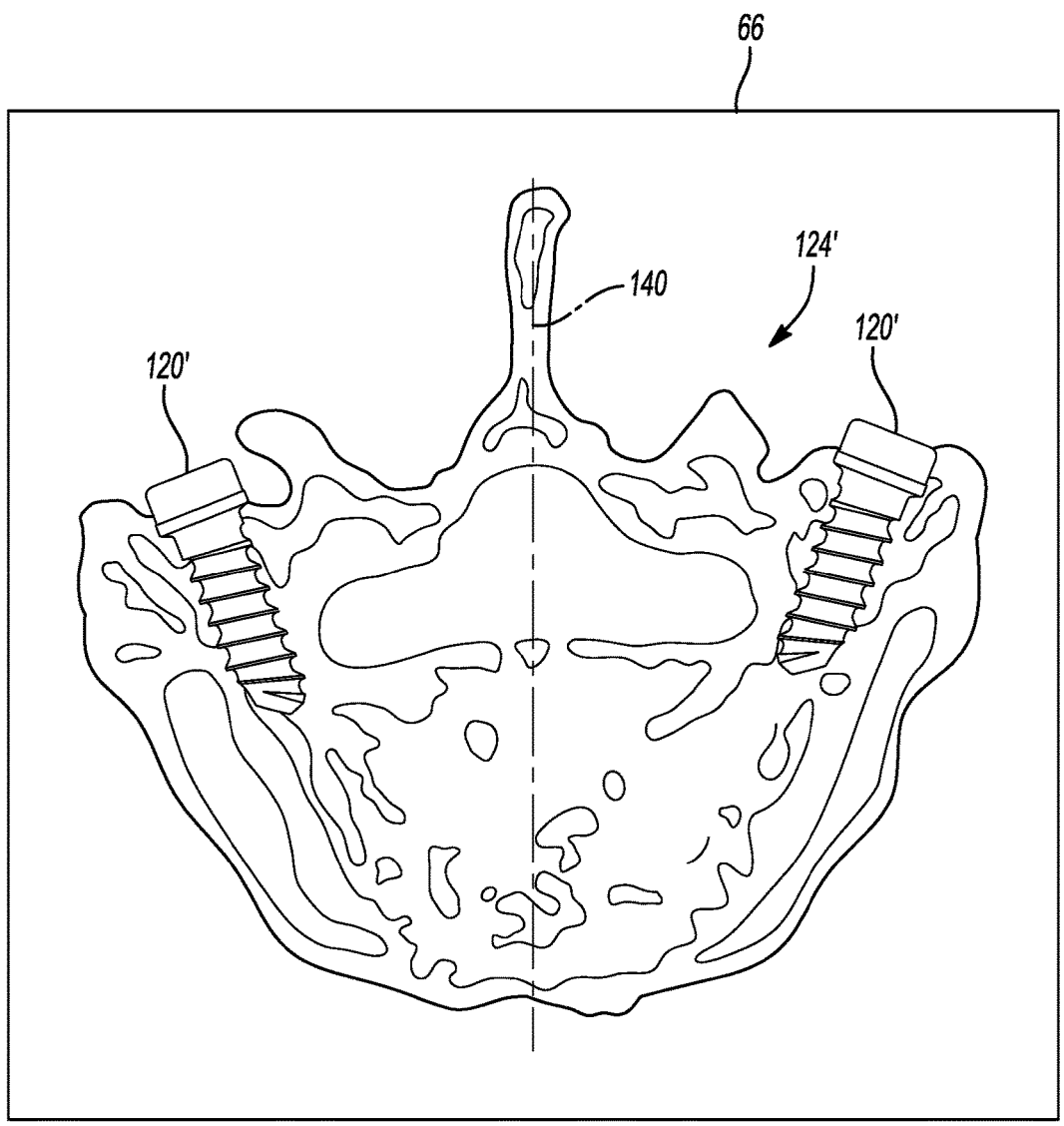
FIG. 7 is a view of a display with image data and an icon of an implant superimposed on the image data.

The tracking device 52 allows the navigation system 10 to determine and illustrate a position of the pedicle screw 120, the implantation instrument 126, or combinations thereof relative to image data acquired of the patient 14. For example, as illustrated in FIG. 7, one or more icons 120i can be superimposed on the first acquired image data 64a, b, c of the patient 14 as the one or more of the pedicle screws 120 is moved towards the vertebra 124 of the patient 14. As discussed above, one or more of the pedicle screws 120, or other appropriate implant members, may be tracked into the patient 14. Further, the instrument or item tracked need not be an implant or a hard tissue implant, but may include a soft tissue implant (e.g. DBS lead). The determined position of the pedicel screw 120 at any appropriate time, such as during or after implantation, may be saved into the navigation memory 62 or other appropriate memory system for later recall. The determined and/or saved position of the pedicle screw 120 may then be used, as discussed herein, for confirmation of the selected procedure or plan for the selected (e.g. surgical) procedure.

As illustrated in FIG. 6, as the pedicle screw 120 moves towards and into the vertebra 124, the icon 120i (in FIG. 7) can be illustrated relative to the image 66. It is understood by one skilled in the art, FIG. 6 illustrates a single one of the pedicle screws 120 prior to insertion into the vertebra 124, while FIG. 7 illustrates two icons 120i to illustrate two individual pedicle screws placed into an image 124' of the single vertebra 124.

The icon 120i can be a preformed model (such as a computer aided drafting figure) of the screw including a priori precise dimension information of the implant, such as the pedicle screw 120. The preformed model can be stored in the navigation memory device 62 and can be accessed by an appropriate processor, such as the navigation processor 60. It is understood, however, that the dimensions of the implant can be determined during the procedure, such as by measuring or using a trackable calibration instrument. The dimensions may then be input to the navigation system 10. It will be further understood, however, that navigation is not required for the performing of the procedure. For example, a low invasive or open procedure may be used to place the implant with no navigational assistance. It will also be understood that the image data 64a of the vertebra can include other information such as a centerline icon 140 that can be automatically or manually determined relative to the image data 64a.

The navigation system 10, by the tracking of the pedicle screw 120 either directly or through a navigated instrument, can be used to illustrate a determined position (including location and orientation) of the pedicle screw 120 relative to the vertebra 124. By illustrating the icon 120i superimposed on the image data 64a,b,c of the patient 14, the user 54 can guide or be given feedback regarding the position of the pedicle screw 120 relative to the patient 14 and the vertebra 124. Accordingly, at a selected time, the user can select to stop driving the pedicle screw 120 into the patient's 14 vertebra 124 based upon the position of the icon 120i or other appropriate information. Later, the tracked icon 120' may be removed when the pedicle screw 120 is not directly tracked by the tracking system or navigation system 10. The position of the pedicle screw 120 may be determined directly based on image data, as discussed herein.

Generally, the imaging system 12 is moved from a position relative to the patient 14 after acquiring the first image data in block 106 and performing the procedure in block 114. For example, the imaging device 12 is moved to allow access to the vertebra 124 for implantation of the pedicle screw 120. The imaging device 12, however, may be moved for any other appropriate reason. As a further example, the imaging device 12 may be moved to allow greater access to a cranium for a DBS placement. It is understood, however, that even when the imaging system 12 is moved that the location of the pedicle screw 120 or other member may be saved within the navigated space. For example, the position of the screw 120 relative to the patient tracker 48 may be saved for recall by the navigation processing unit, or other appropriate processing unit. The position of the pedicle screw 120, for example, may be saved after a selected period of time, such as after implantation or prior to acquiring second image data. The saved position of the pedicle screw 120 may then be recalled to, for example, position the imaging system 12 to acquire the second image data.

Nevertheless, if a second image data is to be obtained the imaging device 12 may be needed to be moved relative to the patient 14. For example, if the imaging device 12 no longer surrounds a portion of the patient's 14 spine, then the imaging device may be moved back to surround a portion of the spine. It may be selected and/or desirable, however, to minimize radiation to which the patient 14 is exposed. As the second image data is generally acquired to confirm a planned procedure, a full 360 exposure to the patient 14 may not be necessary. Thus, as discussed herein the imaging device 12 may be moved relative to the patient 14 to acquire image data that results in less exposure to the patient 14 than the first image data acquired in block 106. For example, a determination, such as with the imager processing unit 58 and/or the navigation processing unit 60

Thus, once the user 54 determines to stop driving the pedicle screw 120 into the vertebra 124, a determination is made of whether a second image data of the subject 14 can be acquired in block 150. The second image data acquired of the patient 14 can be image data that is acquired with the imaging system 12, or any appropriate imaging system, of the patient 14 after the pedicle screw 120 is positioned within the vertebra 124 to a selected amount or distance.

The second image data may be illustrated, as discussed herein, for use by the user 54. The second image data may also be augmented with various information, such as a model of the implant. For example, second image data may have a model of an implant that is superimposed thereon based on tracking information, as disclosed in U.S. Pat. No. 8,842,893, issued on Sep. 23, 2013, titled "Method and Apparatus For Image-Based Navigation", incorporated herein by reference. As discussed above, the model of the implant may be used to assist in navigation. Further, selected measurements of the implant may be acquired. Nevertheless, the image data of the patient 14 may be used to assist in performing and/or confirming the procedure being performed on the patient 14.

With continuing reference to FIG. 2 the determination of whether to acquire second image data in block 150 may be for various purposes including confirming a procedure, determining a current location of an implant (e.g. the position of the pedicle screw 120), determining further procedure steps, or for other appropriate reasons. As an example, in the following discussion, it may be selected to confirm that the implant 120 has reached or been positioned in a planned position into the vertebrae 124. However, if it is desired or determined that confirmation image data is not needed, a NO path through block 152 may be followed and the process may END in block 154. For example, if an open procedure is performed, a confirmation image may not be selected or necessary at a selected time. Further, other confirmation techniques may be employed that do not include acquiring second image data of the subject 14.

Nevertheless, a second image data may be selected in the block 150 and a YES path can be followed through YES block 160. The determination in block 150 may be automatically or by input of a user. For example, the procedure may be included as a program that is executed by the navigation processing unit 60 and a prompt for second image data may be given.

After the YES block 160 is determined, however, from block 150, a determination block of whether the patient tracker 48 is attached to the patient 14 in block 162 may be determined. The determination of whether the patient tracker is still attached in block 162 may also be manual or automatic. For example, the user 54 may input to the system, such as using the keyboard 70, that the patient tracker is attached. Further, or alternatively thereto, the system, such as including the tracking system 29 and the navigation system 10, can determine whether a signal is received or being measured from the patient tracker 48 attached to the patient 14. If the patient tracker 48 is determined to still be attached, then a yes path is followed through YES block 163. The tracking system 29 and navigation system 10 can track the patient 14 and the imaging system 12 such as with the imaging system tracking device 50. When tracking, the navigation system 10 may then determine the position of the patient 14 and the imaging system 12 for various purposes, such as acquiring additional image data, including confirmation image data. Further, as discussed above, the position of the implant, for example the pedicle screw 120, may have been determined by tracking the position of the pedicle screw 120 such as with the instrument tracker 52 during the procedure. The position of the implant 120, therefore, may be known and recalled from the navigation memory 62. The saved position of the pedicle screw may be from when the pedicle screw 120 was tracked during implantation and the position of the pedicle screw 120 was saved into the navigation memory 62.

As illustrated in FIG. 1, the imaging device 12 can be positioned relative to the patient 14 to acquire the first image data in block 106. However, in performing a procedure, such as placing the pedicle screw 120, the imaging device 12 may be moved away from the patient 14. If moved away from the patient 14, the patient 14 is repositioned relative to the imaging device 12 for acquiring second image data. Generally, the imaging device 12 may be moved near the patient 14 or the patient 14 may be moved near the imaging device 12. During movement the exact positioning of the imaging device 12 relative to the patient 14 may have changed from when the first image data was acquired.

A three dimensional model of the patient 14, or at least a portion of interest or anatomy of interest of the patient 14, may be produced for viewing on the display 66 from the first image data. The first image data, therefore, may require many projections (e.g. about 300 to about 700 projections, generally each acquired at different positions) through the patient 14 to acquire sufficient image data to generate the three-dimensional model of the patient 14. When acquiring the second image data, however, it may not be necessary or selected to acquire as many projections as during acquiring the first image data. The second image data may be selected for verification or confirmation of implant placement, and model creation, thus less image data may be necessary. Thus, acquiring minimal projections through the patient 14 can minimize or reduce the amount of radiation experienced by the patient 14 and the user 54.

The second image data, therefore, may include selecting a selected number or minimal projections through the patient 14 may be made. The second image data may also be referred to as confirmation or verification image data. Thus, determining appropriate or best positions of the imaging device to acquire the second image data may assist in minimizing the number of projections or views needed. Each projection may require an exposure to radiation, such as x-ray radiation to acquire image data of the subject 14. In particular, the imaging device 12 may be operated to acquire views in the second image data to determine the position of the implanted member, such as the pedicle screw 120, with a selected number, such as a small number including two, projections through the patient 14. The determined position of the implant from the acquired second image data can be used to generate an icon for superimposing on the first acquired image data or model generated therefrom, as discussed herein.

By maintaining tracking of the patient 14 with the patient tracking device 48, the imaging device 12 can be tracked with the tracking device 50 to position the imaging device 12 relative to the patient 14 to acquire the minimal or selected number of projections while acquiring enough image data to appropriately view the implant 120. For example, in block 164 a recall of the position of the imaging device during acquisition of the first image data from block 106 may occur.

The recalled position of the imaging device from block 164 may assist in a determining one or more positions of the imaging device for acquiring the second image data in a block 165. In particular, a relative position of the imaging device 12 and the patient 14 may be determined for acquiring the second image data. The relative position may be based on the recalled position for acquiring the first image data from block 164. Further, in determining relative positions for acquiring the second image data in block 165, the recalled position of the implant member, such as the pedicel screw 120 may also be made. The tracked position of the pedicle screw 120 may be used to assist in determining appropriate or optimal positions for acquiring the second image data. As discussed herein, optimal positions of the imaging device for acquiring the second image data may be imaging as many views and/or as much of the implanted devices as possible in each view. Further, the optimal positions may include minimizing or reducing overlap of multiple implants in a single view and/or overlap of selected anatomical features or structures. This may allow for a minimal number of views for confirmation of the position of the pedicle screw 120, or other implant, according to the plan and/or selected procedure from block 104. Thus, at least because the implant is tracked and the implant's location relative to the patient 14 is known, a position for the imaging device to acquire image data of the implant can be determined.

The determination of the positions in block 165 may be determined with the processing unit, including the navigation processing unit 60, by executing instructions to determine selected positions of the imaging device to acquire the second image data. The determined position of the imaging device may be to ensure imaging of at least more than one implant in each view or projection when acquiring the second image data. Thus, an implant may be unobstructed by a second implant in the acquired second image data. Further, the determined relative positions may include positioning the imaging device 12 according to any of the possible positions of the imaging device 12 including, rotation, sway, wag, axial movement, and transverse movement relative to a long axis of the subject 14.

Therefore, if the YES path 163 is followed the imaging device 12 can be moved and/or tracked in block 166. Also the patient can be moved and/or tracked in block 168. While tracking the patient in block 168 and tracking the imaging device in block 166, the imaging device can be moved to one or more selected positions, which may allow for acquiring image data at one or more perspectives or views, relative to the patient 14 in block 170. The positions may be determined in block 165 and the patient and/or imaging device may be moved in block 170.

With continuing reference to FIG. 2 and additional reference to FIGS. 8 and 9, the imaging device 12 that includes the source 26 and the detector 28 can be moved relative to the patient 14 including the vertebrae 124. The imaging device 12 may be moved to acquire selected images for the second image data. The second image data may be optimal or procedurally optimal positions of the imaging device 12 to acquire the second image date with a minimal number or selected number of projections. The selected number may be a number appropriate or adequate for a confirmation of the selected and planned procedure. The selected and planned procedure may be a selected location for implantation of the pedicle screw 120.

FIG. 8 schematically illustrates the source 26 in various locations 26', 26", and 26''' relative to the detector in various locations 28', 28", and 28'''. Further the imaging device tracking device 50 is illustrated in various positions 50', 50" and 50'''. The tracking device locations 50', 50", 50''' can be used to track and determine location of the source at the various locations 26', 26" and 26''' and/or the detector at various locations 28', 28", and 28''' for generating views relative to the vertebrae 124. The source 26 can emit x-rays through the patient 14 to create image data at the detector 28, as is generally understood in the art. Each of the projections can create a view as illustrated as view A, view B, and view C in FIG. 9 relative to the position of the source 26', 26" and 26''', respectively illustrated in FIG. 8.

As noted above, in block 165 the navigation system 10 can be used to automatically determine the positions of the source 26 relative to the patient 14 to acquire views that would acquire image data of all of the implants positioned and their relative locations to each other. Therefore, in block 176 acquire second image data at a selected number of positions of the imaging system 12 occurs. The views may refer to or be at positions that are determined in block 165. The views can include acquiring one or more views or projections for illustrating or determining the position of the implant relative to the subject 14. Thus, the second image data may include a plurality of views from a plurality of positions of the imaging device 12. For example, two or more views may be acquired of the subject 14 for the second image data.

With continuing reference to FIG. 2 and reference to FIGS. 8 and 9, at View A the source 26' can be tracked with the image tracking device 50' and x-rays can be projected through the vertebrae 124 to the detector 28'. The image data acquired can be displayed or saved and can include a view 180 that illustrates or includes image data of a first pedicle screw 120a and the second pedicle screw 120b. Specifically the image of View A can include an image 120a' of the first pedicle screw and an image 120b' of the second screw. As both of these screws 120a, 120b can be viewed in the View A 180 a determination of geometry and position of the screws may be collected from View A.

Additionally, the imaging device 12 can be operated to move the source to source position 26" by tracking the tracking device 50". For example, the navigation processing unit 60 can be used to provide coordinates for positioning the imaging device 12 and/or directly control the imaging device 12. Regardless, a projection of x-rays can then be made through the vertebrae 124 and the two screws 120a, 120b may be imaged at the detector at the position 28". View B 184 can also include image data of the two screws 120a, 120b in a different perspective, as imaged at 120a" and 120b", from the View A 180. The two views 180, 184 can be used to create a calculation of a position of the two screws 120a, 120b, relative to the vertebrae 124 which is also included in the image data as vertebra image 124' and 124". It is understood, as discussed above, that movements of the detector 28 and/or source 26 may include more than rotational movement and may also include linear movements along or transverse to a long axis of the subject 14.

As illustrated in FIG. 9 the images 180, 184 include image data of both of the implanted pedicle screws 120a, 120b and show them in varying perspectives. Therefore, appropriate algorithms may be executed with the navigation processing unit 60, or other appropriate processing unit, to determine a position of the screws relative to the anatomy, including the vertebra 124. In addition, the geometrical configurations and sizes of the screws 120a, 120b can be stored in the navigation memory 62 and recalled to assist in determining the position of the screws 120b and 120a in the vertebrae 124.

A determination of a position the implant in the second image data is made in block 182. The determination may be made with one or more processing units, such as the imaging processing unit 58 or the navigation processing unit 60. The selected processing unit may execute selected instructions to determine the position of the members within the second image data in block 182.

The determination or identification of the implant, such as the pedicle screw 120 in the second image data may include various processing steps. For example, a user may identify a seed point in one or more of the views or projections. Further, the pedicle screw may include a selected pixel or voxel contrast or brightness. In either situation, various region growing techniques may be used to segment the pedicle screw 120 from the image. Thus, the process may include segmenting the image data from a selected seed point.

The seed point may also be determined (i.e. automatically determined by executing instructions with a processor) or selected based on the known or recalled determined implanted position. As discussed above, the pedicle screw 120 may be tracked as it is implanted and the implanted position may be saved. The saved position may be recalled in block 164 or block 165 by a processor, such as the navigation processor. The recalled position may also, therefore, be used in determining a location of the pedicle screw 120 for segmentation from the image data acquired at the second image data or a portion of the second image data (such as a single view). The recalled position of the pedicle screw 120 may be used to determine a selected point, such as a point at a center of the pedicle screw 120. In various embodiments, the processor that recalls the saved position may use the saved position to determine a seed point in the image data. The geometry of the pedicle screw 120 may also be stored in the memory 62 and recalled. Thus, segmentation and determination of the position of the screw in the image data may begin with a point at known center of the saved geometry of the pedicle screw 120.

Illustrating a position of the implant, including the screws 120a, 120b, based on the second image data can be performed in block 188. The position of the screws 120 may be illustrated on the first image data from block 106, a model based on the imager data from block 112, or the second image data from block 176. The position of the screws 120 in the first image data block 106 or the processed model from block 112 may be based on the determined position of the screws 120 in block 182. Moreover, the determined position of the member 120 for illustration superimposed on or relative the first image data block 106 or model form block 112 may be based only on the determination of the position of the screws in block 182 in the second image data.

In various embodiments, if the screws are to be illustrated on the first image data acquired in block 106 or on a model generated with the first image data, the second image data acquired in block 176 may be first registered to the first image data or the model in block 179. In registering the first image data to the second image data, points in one of the two image data are correlated or mapped to a point in the other image data. The second image data may be registered to the first image data using various techniques, such as known in the art regarding two-dimensional (2D) to three-dimensional (3D) registration techniques. In various embodiments, boney features or structures that may be present in both the first image data and the second image data may be identified (e.g. manually or automatically) and extracted in both of the first and second image data. The extracted features or structures may be matched and used for registration and mapping. In addition or alternatively, the second image data may be registered to the first image data based on the recalled position of the imaging device from block 164. Thus, the position of the second image data may be known relative to the position of the first image data and registration may occur.

The position of the pedicle screw 120 may be determined in the second image data, as discussed above. Through the registration, the position of the pedicle screw may then be mapped or determined in the first image data. This registration, therefore, may allow the determined position of the pedicle screw 120 from the second image data to be placed or illustrated in the first image data and/or the model that is based on the first image data.

The determined positions of the screws 120a, 120b may be ill-used as icons representing the screws can be superimposed at the determined positions on the models that may be generated, such as in the process image data block 112, based on the acquired first image data in block 106. The acquired second image data from block 176 need not be used to create a new model or may not be viewed directly by the user 54, but may be used by the imaging processing unit 58 or the navigation processing unit 60 to generate a view, such as with the icons 120q (FIG. 10) for viewing by the user 54 on the models created with the acquired first image data from block 106. Based upon the above described, the user 54 can view the implanted position of the implant 120a, 120b relative to the acquired first image data, which also may be used to generate a plan.

In other words, the determined position of the pedicle screw 120 (again it is understood by one skilled in the art that any member may be imaged) may be made based upon the second image data acquired in blocks 176, 302. According to various embodiments, the position of the pedicle screw 120 may be determined substantially only or only based upon the second image data. The determined position may then be displayed relative to the first image data and/or a model based on the first image data. The model may include a 3D model of the selected region of the patient 14. The 3D model based on the first image data may include a 3D rendering from a plurality of 2D slices or projections or other appropriate first image data. Regardless, registration of the second image data to the first image data may allow a representation of the pedicle screw 120 to be displayed on the first image data or model. Because the second image data follows the procedure, the determined position of the pedicle screw 120 in the second image data may be used as a confirmation of the procedure when the pedicle screw 120 is illustrated on the first image data.

Figure 10:
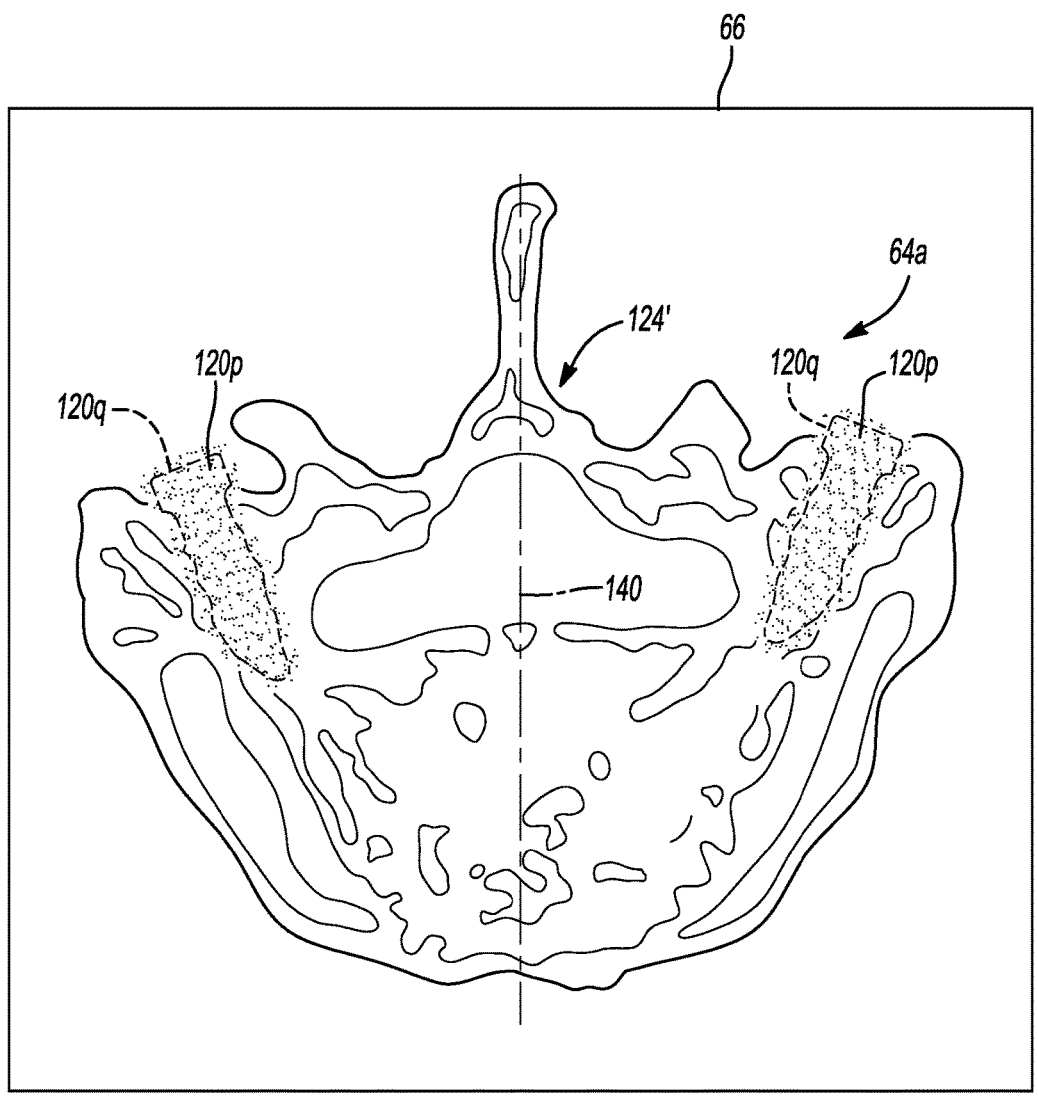
FIG. 10 is a screen shot of an illustrated position of an implant based on image data.

With reference to FIG. 10, the image 124' of the vertebra 124 can be generated using the first acquired image data from block 106. A plan icon 120p can be illustrated relative to the image 124'. The plan icon may include a planned or selected position for one or more implants based on the first acquired image data from block 106. The plan icon 120p may be a precise 2D or 3D model of the selected implant or may only be a geometrical representation of a selected implant. After the second image data is acquired in block 176, a confirmation icon 120q may be illustrated relative to the image 124' in addition to the plan icons 120p or alternatively thereto. As discussed above, the second image data may be registered to the first image data to allow the determined position of the pedicle screw 120 to be illustrated superimposed on the image 124'.

Therefore, the user 54 can view the confirmation icons 124q at positions determined, at least in part or in whole, by the second image data acquired in block 176. In other words, the position of the pedicle screw 120 in the second image data may be based upon analysis of the second image data (e.g. based on segmentation of the pedicle screw from the second image data). The position of the second image data to the first image data may then be used to illustrate the determined position of the pedicle screw on the first image data. As noted above, the confirmation icons 120q may be superimposed on the image data relative to the plan icons 120p so that both are superimposed on the image data 124'. Therefore, the second image data may be used to illustrate confirmation icons 120q relative to the image data 124' that can be used to generate an initial plan for a procedure.

For reference, with reference to FIGS. 8 and 9, a View C may be generated when the source 26 is at source position 26''' and may be tracked with the tracker 50 at tracker position 50'''. At the View C position, the source 26 projects x-rays through the vertebra 124 to the detector position 28''. The View C 190, illustrated in FIG. 9, may include a view of only one screw, even though two are present. One of the two screws may obscure the other screw. Thus, at least one of the screws may be obstructed by another screw in the View C. Therefore, View C may not provide appropriate information for determining a position of the implants, including the screws 120a, 120b. In other words, View C may be obstructed or obscured (e.g. at least one item of interested, such as one of the pedicle screws, is at least partially obscured or obstructed by another one of the pedicle screws) while View A and View may be unobstructed or unobscured views. The unobstructed views allow for a determination of all or most of the members with fewer projections, including radiation exposures, through the patient 14.

Tracking the imaging device 12 with the imaging device tracking device 50, thus, may assist in moving the imaging device to effective and efficient positions for acquiring the second image data. This determination in block 165 may reduce the number of exposures needed to acquire enough image data to make a determination of positions of the implants. Thus, acquiring the second image data according to the method 100 may require a minimal amount of views or projections that include a high discrimination of position information of the implants relative to the vertebrae 124. This can ensure that a less discriminatory view, such as View C 190, is not or need not be acquired and therefore not exposing the patient to x-rays when acquiring such a view.

As discussed above, a determination can be made in block 162 whether a patient tracker is still attached to patient 14. If a patient tracker is not attached, then a no path to NO block 200 may be followed. The imaging device 12 may still be moved relative to the patient 14 during a procedure on the patient, such as implantation of the pedicle screws 120, and the imaging device 12 may be again moved relative to the patient 12 to acquire the second image data it is determined to be acquired in block 150. When the patient is no longer tracked with the patient tracking device 48 at least one test image data projection or view can be acquired of the patient 14 to assist in determining appropriate positions for the imaging system 12 relative to the patient 14 to acquire a minimal number of projections through the patient 14 to determine the position of the implant, as discussed above.

When following the no path through NO block 200, the imaging device 12 can be moved relative to the patient 14 to a imaging device first test position in block 202. The imaging device test position can be any appropriate position relative to the patient 14 and may include both a positioning of the gantry 20 and a selected location of the source 26 and the detector 28. At the first test position a first test image data may be acquired in block 204. The first test image data can be an image data acquired as a projection taken through the patient 14 at the first test position.

The image data acquired at the first test position at block 204 can be processed with an appropriate processing unit, such as the image processing unit 58 or the navigation processing system 60, to determine a position of the implants 120 in the acquired first test image data. The determination of the orientation and location of the implants 120 in the first test image data allows for a determination of one or more positions for acquiring second image data in block 208. It is understood, however, that the first test image data may also be used as a view or projection of the second acquired image data. Further, the determination of one or more positions for acquiring second image data in block 208 may be based only on the acquired first test image data in block 204. Thus, a tracking of the imaging device 12 relative to the patient 14, including the patient tracker 48, is not necessary to for the determination of one or more positions for acquiring second image data in block 208.

The first test image data may be used to determine positions of the imagining device to acquire second image data. Thus, rather than tracking the imaging device 12, as discussed above, the first test image data may be analyzed to determine appropriate positions for acquiring the second image data. In the determine positions for acquiring the second image data in block 208, the first test image data may be evaluated to determine the positions of the implants therein and relative to the patient 14. The first test image data, however, may not include enough image data to fully determine positions of all of the implants 120. Thus, the determined positions in block 208 may allow for acquiring the second image data with the imagining device 12 at a minimum number of positions to acquire a minimum number of projections to determine the position of the implants, as discussed above.

Analyzing the first test image data can be done in a manner similar to processing the image data to generate a model, as is generally understood in the art, and allows for determining the position of the implants in the first test image data. Therefore, the determination of the location for acquiring the second image data in block 208 can be performed without tracking the patient 14 with the patient tracker 48 or tracking the imaging device 12 with the imaging device tracking device 50. As the location and orientation of the implant 120 is determined in the first test image data, the determination of location for acquiring second image data can be based thereon.

Further, procedure information may also be input automatically or by the user or recalled from the plan that is saved in the memory 62. For example, a number of implants and selected relative position of the implants may be used to assist in determining positions in block 208. For example, if a first test image includes only two implants, but it is known that four implants were placed, the processor may determine a relative position of the two implants in the image to determine a likely position of the other two implants. Further, if an axial view imaged only two implants, a selected oblique view may be selected to image all four of the implants. The determining of the positions of the imaging device may be automatically determined by the processor based on the recalled information and analysis of the first test image data. Further, the positions of the implants may be recalled by the processor system form the memory system.

Once the determination for location of acquiring the second image data in block 208 is completed, the imaging device 12 can be moved to the determined one or more positions relative to the subject in block 300. Second image data can then be acquired at the one or more positions in block 302 in a manner similar to acquiring second image data in block 176. Once the second image data is acquired at the determined one or more positions in block 302 the position of the pedicle screws 120 may be determined in the second image data in block 182, as discussed above (e.g. by segmentation of the pedicle screws form the second image data). The second image data may also be registered to the first image data in block 179, as also discussed above. In various embodiments, registration may occur by feature or structure extraction and registration between the first and second image data. The determined position of the pedicle screws can be illustrated on the second image data or the first image data in block 188, as discussed above.

After illustrating the position of the implant 120 on the image data, such as the first image data or model formed using the first image data in block 188, the method can end in END block 154. As discussed above, the imaging system 12 can be used to acquire the second image data to assist in illustrating a location of the implant for confirmation of a planned procedure. Further the illustration of the implant based upon the second image data can assist the user 54 in determining whether additional procedure steps, such as surgical steps, may be selected to be performed to achieve a plan or augment the plan based upon the user's expertise. Accordingly, the second image data is used to assist in performing a procedure on the patient 14 to either achieve a plan or achieve a selected result. It is understood, however, that the second image data can be acquired of any appropriate subject and need not be limited to a human subject as illustrated in FIG. 1.

The method illustrated in FIG. 2, therefore, allows for acquiring a second image data without acquiring a complete set of image data. As is understood by one skilled in the art, a selected amount of image data (such as a complete set) can be used to generate a three dimensional model of the patient 14. The first image data acquired in block 106 can be enough image data to generate a selected quality of a model of the patient 14. The amount of the first image data, therefore, may include acquiring at least 300 projections of the patient 14 as the x-ray beam (between the source 26 and the detector 28) move arounds the patient 14 via the gantry 20. The second image data may include a single acquisition of multiple acquisitions, but both generally being less than the first image data acquisition projections. For example, a test image data acquisition may include about 1 to about 3 projections. The second image data (based on the test image data or not) may then include about 10 projections or less at oblique angles around the patient 14, such as by moving a x-ray beam. The second image data, however, may be optimized to view angles to register or verify the position of the implanted hardware relative to a prior image data, such as pre-operative image data including in the first image data. Therefore, the second image data can be minimized relative to the first image data yet still allow for providing image data for confirmation of a selected plan or assisting in completing a surgical procedure on the patient 14 as discussed above.

The second image data (acquired in either blocks 176 or 302) may be the only data used to determine the position of the pedicle screws 120 (or other members that are imaged). Further, the second image data may be the only data used to determine the position of the members relative to the first image data from block 106 or a model formed therefrom in block 112. Thus, the second image data may be used without or in the absence of tracking information to confirm a position of the members 120 relative to the patient 14. Also, as discussed above, the position of the members determined in block 182 may be illustrated or superimposed on the first image data from block 106 or model from block 112.

Further, the members 120 need not be placed in a hard tissue, such as a boney tissue. The member that is implanted may be placed into soft tissue, such as a deep brain stimulation probe or electrode. The placement of the electrodes may be planned and image data may be acquired after a selected portion of the procedure. A position of the member may be determined in a second image data and an icon representing the member may be superimposed as discussed above. Further, the imaging device may be tracked and/or a test image may be acquired to determine a position of the imaging device for acquiring second image data. Thus, one skilled in the art will understand that the member placed in the subject need not be placed in hard or boney tissue.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of confirming at least a portion of a procedure with image data acquired with an imaging device, comprising:
    moving the imaging device to a selected position relative to a portion of interest;
    acquiring confirmation image data of the portion of interest;
    determining a position of a member within the confirmation acquired image data; and
    superimposing an icon representing the member on a model generated with prior acquired image data;
    wherein the prior acquired image data is acquired prior to the confirmation image data;
    wherein a position of the icon is based upon the determined position of the member in the confirmation image data.

2. The method of claim 1, further comprising:
    tracking a position of the member into the portion of interest; and
    tracking a position of the imaging device relative to the portion of interest.

3. The method of claim 2, wherein tracking the position of the imaging device relative to the portion of interest includes:
    tracking a detector of the imaging device while moving the detector to a first position relative to the portion of interest for acquiring confirmation image data of the portion of interest and the member; and
    tracking the detector of the imaging device while moving the detector to a second position relative to the portion of interest for acquiring confirmation image data of the portion of interest and the member.

4. The method of claim 3, wherein tracking the detector includes:
    recalling from a memory system a saved position of the imaging device during at least a portion of time when acquiring the prior acquired image data;
    determining a position of the detector to acquire unobstructed image data of the member in a first projection to allow determining the position of the member within the acquired confirmation image data;
    instructing the detector to move to the determined position;
    wherein both the prior acquired image data and the confirmation image data may include a plurality of projections, wherein each of the plurality of projections is at a different position of the detector.

5. The method of claim 4, further comprising:
    executing instructions with a processing unit to generate the model of the portion of interest generated with the prior acquired image data; and
    executing instructions with the processing unit to model the position of the member for superimposing the icon representing the member at the determined position on the model of the portion of interest.

6. The method of claim 1, further comprising:
    acquiring a test image of at least a first portion of the portion of interest including the member;
    evaluating the acquired test image by extracting the member from the acquired test image data;
    determining a position of the member within the portion of interest based only on the evaluation of the acquired test image; and
    executing instructions with a processing unit based on the determined position of the member to determine at least one position for the acquiring confirmation image data of the portion of interest to at least minimize overlap of at least one of different implants or different anatomical features.

7. The method of claim 6, wherein executing instructions with the processing unit to determine at least one position for acquiring confirmation image data of the portion of interest based on the determined position of the member includes determining the position of the imaging device to acquire an unobstructed view of the member.

8. The method of claim 6, wherein moving the imaging device to the selected position relative to a portion of interest is based on executing instructions with a processing unit to determine at least one position for acquiring confirmation image data of the portion of interest based on the determined position of the member.

9. The method of claim 6, further comprising:
executing instructions with the processing unit to determine the position of the icon superimposed on the model.

10. The method of claim 9, further comprising:
displaying with a display device the model with the icon superimposed thereon.

11. The method of claim 1, wherein determining the position of the member within the acquired confirmation image data includes determining the position of the member relative to the model based only the acquired confirmation image data.

12. A system for confirming at least a portion of a procedure with image data, comprising:
an imaging device configured to be moved to a selected position relative to a portion of interest of a subject and acquire confirmation image data of the portion of interest of the subject;
a processor system configured to execute instructions to:
evaluate the acquired confirmation image data of the portion of interest of the subject acquired with the imaging device, and
determine a position of a member based on the acquired confirmation image data of the portion of interest of the subject; and
a display device configured to display an icon representing the member superimposed on prior acquired image data;
wherein the prior acquired image data is acquired prior to the confirmation image data;
wherein a position of the icon is based upon the determined position of the member in the confirmation image data.

13. The system of claim 12, further comprising:
the member configured to be imaged with the imaging device at the portion of interest in the subject.

14. The system of claim 13, further comprising:
a navigation system having a tracking system configured to track a first tracking device associated with the imaging device and a second tracking device associated with the subject.

15. The system of claim 14, further comprising:
a memory system configured to store a relative position of the imaging system and the portion of interest while acquiring the prior image data.

16. The system of claim 15, wherein the processor system is further configured to execute instructions to:
recall the stored relative position of the imaging system and the portion of interest while acquiring the prior image data; and
determine at least one position of the imaging device to acquire the confirmation image data of the member that is unobstructed image data based at least one of the recalled stored relative position of the imaging system, the portion of interest while acquiring the prior image data, or a tracked position of the member.

17. The system of claim 13, wherein the processing system is further configured to execute instructions to:
evaluate a first test image data to identify the member; and
determine at least one position of the imaging device to acquire the image data of the portion of interest acquired with the imaging device.

18. The system of claim 12, wherein the processing system is further configured to execute instructions to determine the position of the member based only on the acquired confirmation image data of the portion of interest of the subject.

19. A method of confirming at least a portion of a procedure with image data acquired with an imaging device, comprising:
acquiring a first image data of at least a portion of interest of a subject with the imaging device at a first position relative to the subject;
moving the imaging device from the first position;
operating a first processing unit to determine a second position of the imaging device relative to at least the portion of interest of the subject to acquire a second image data after a member has been implanted into the subject;
moving the imaging device to the second position relative to the portion of interest;
acquiring the second image data of the portion of interest with the imaging device at the second position;
operating a second processing unit to:
(i) determine a position of a member within the acquired second image data, and
(ii) determine a first image data position of the member based on the determined position of the member within the acquired second image data; and
viewing a display of an icon superimposed on the first image data representing the member at the determined first image data position.

20. The method of claim 19, wherein the first image data includes a model of the portion of interest of the subject and the icon is superimposed on the model.

21. The method of claim 19, further comprising:
storing coordinates of the first position of the imaging device; and
recalling the stored coordinates of the first position;
wherein operating the first processing unit to determine the second position of the imaging device relative to at least the portion of interest of the subject to acquire the second image data is based at least on the recalled stored coordinates.

22. The method of claim 19, further comprising:
acquiring a first test image including the member; and
operating the first processing unit to determine a position of the member in the first test image data relative to the subject;
wherein operating the first processing unit to determine the second position of the imaging device relative to at least the portion of interest of the subject to acquire the second image data is based at least on the determined position of the member.

23. The method of claim 22, further comprising:
implanting the member into the subject.

* * * * *